United States Patent [19]

Colle et al.

[11] Patent Number: 4,704,398

[45] Date of Patent: Nov. 3, 1987

[54] TRIAZOLYL-KETO-DERIVATIVES ENDOWED WITH A FUNGICIDAL ACTIVITY

[75] Inventors: Roberto Colle, Basiglio; Giovanni Camaggi, Lodi; Franco Gozzo, S. Donato Milanese; Walter Visentin; Luigi Mirenna, both of Milan, all of Italy

[73] Assignee: Montedison S.p.A., Milan, Italy

[21] Appl. No.: 687,282

[22] Filed: Dec. 28, 1984

[30] Foreign Application Priority Data

Dec. 30, 1983 [IT] Italy .................. 24438 A/83

[51] Int. Cl.$^4$ .................. C07D 249/08; A61K 31/41
[52] U.S. Cl. .................. 514/383; 548/262
[58] Field of Search .................. 548/262; 546/276; 514/383, 340

[56] References Cited

U.S. PATENT DOCUMENTS 4,316,932  2/1982  Kranz et al. .................. 514/383

FOREIGN PATENT DOCUMENTS 0123319  10/1984  European Pat. Off. .................. 548/262
2081709   2/1982  United Kingdom .................. 514/383
2118175  10/1983  United Kingdom .................. 548/262
2121042  12/1983  United Kingdom .................. 548/262

Primary Examiner—Glennon H. Hollrah
Assistant Examiner—D. L. Dinner
Attorney, Agent, or Firm—Stevens, Davis, Miller & Mosher

[57] ABSTRACT

Described herein are α-(1-triazolyl)-keto-derivatives of general formula:

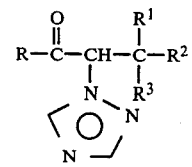

wherein R is phenyl or heteroaryl, optionally substituted, alkyl; $R^1$ is alkoxyl, optionally substituted aryloxy, alkyl, alkenyl, alkynyl, alkoxyalkyl, alkoxycarbonyl, cyano, optionally substituted phenyl, or, along with $R^2$, an alkylidene; $R^2$ is H or, along with $R^1$, an alkylidene; $R^3$ is alkylcarbonyl, alkoxycarbonyl, arylcarbonyl, cyano or alkoxyalkylcarbonyl; such compounds being endowed with a high fungicidal activity.

6 Claims, No Drawings

TRIAZOLYL-KETO-DERIVATIVES ENDOWED WITH A FUNGICIDAL ACTIVITY

BACKGROUND OF THE INVENTION

Triazolyl derivatives endowed with a fungicidal activity are known in literature; for example, British patent application No. 1,511,956 (Imperial Chemical Industries) described triazolyl-diketo-derivatives of general formula:

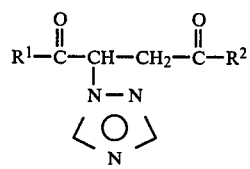

in which $R^1$ and $R^2$, like or unlike each other, may be cycloalkyl, alkyl or phenyl, these groups being optionally substituted.

THE PRESENT INVENTION

We have now found-and that being the objecy of the present invention-α-(1-triazolyl)-keto-derivatives having general formula:

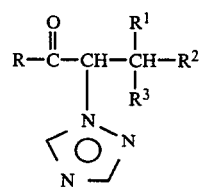

in which:

R is a phenyl optionally substituted by one or more groups selected from alkyl $C_1$-$C_4$, alkynyl or haloalkynyl $C_2$-$C_3$, halogen, nitro and phenyl; a heteroaryl selected from the group consisting of 2-furyl, 2-thienyl, 2-pyridyl, 3-pyridyl, 4-pyridyl and optionally substituted by one or more groups selected from alkyl $C_1$-$C_4$, alkynyl $C_2$-$C_3$, haloalkynyl, halogen, nitro and phenyl; an alkyl $C_1$-$C_4$;

$R^1$ is an alkoxyl $C_1$-$C_4$; an aryloxy in which the aryl moiety is a phenyl optionally substituted by one or more groups selected from amongst alkyl $C_1$-$C_4$, alkynyl or haloalkynyl $C_2$-$C_3$, halogen, nitro and phenyl; or $R^1$ represents, along with $R^2$, an alkylidene of formula (=CHR$^4$), wherein $R^4$ is hydrogen or alkyl $C_1$-$C_4$; or also when R represents a phenyl substituted by phenyl, alkynyl or haloalkynyl $C_2$-$C_3$, or a heteroaryl group, as specified hereinbefore, $R^1$ may be also an alkyl $C_1$-$C_4$; an alkenyl $C_2$-$C_4$; an alkynyl $C_2$-$C_3$; an alkoxyalkyl having from 1 to 4 carbon atoms in both the alkoxyl moiety and the alkyl moiety; an alkoxycarbonyl with 1 to 4 carbon atoms in the alkoxyl moiety; a cyano; a phenyl optionally substituted by one or more groups selected from alkyl $C_1$-$C_4$, alkynyl or haloalkynyl $C_2$-$C_3$, halogen, nitro and phenyl;

$R^2$ is a hydrogen or, along with $R^1$, an alkylidene =CHR$^4$ wherein $R^4$ is H or alkyl $C_1$-$C_4$;

$R^3$ is an alkylcarbonyl having from 1 to 4 carbon atoms in the alkyl moiety; an arylcarbonyl in which the aryl moiety is a phenyl optionally substituted by one or more groups selected from alkyl $C_1$-$C_4$, alkynyl $C_2$-$C_3$, haloalkylinyl, halogen, nitro and phenyl; an alkoxyalkylcarbonyl having from 1 to 4 carbon atoms both in the alkoxyl moiety and in the alkyl moiety.

The compounds of formula I are endowed with a high fungicidal activity and with other useful properties, described hereinafter, which permit the use thereof in the agrarian field in the defence of useful plants from the infestation due to phytopatogenous fungi.

Another object of the present invention resides in the use of the compounds of formula I as fungicide in the agrarian field, and the fungicidal compositions containing such compounds as an active substance.

In the description of the synthesis processes for preparing the compounds of formula I given hereinbelow, the symbols R, $R^1$, $R^2$ and $R^3$ have the same meanings indicated for formula I.

Useful synthesis methods for obtaining the compounds of formula (I) when $R^2$=H, are the following (equations 1, 2 and 3);

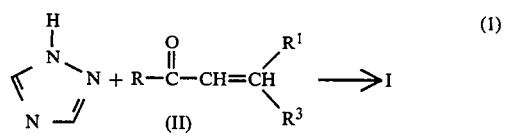

Reaction 1 is conducted in an inert solvent such as an aromatic hydrocarbon, for example toluene, in the presence of a catalytic amount of an organic base, for example a tertiary amine.

As an alternative, the reaction can be carried out in a polar solvent such as dimethylformamide or ethanol in the presence of an inorganic base such as an alkaline carbonate or hydroxide, in particular potassium hydroxide.

The compounds of formula II are known compounds or they are easily preparable according to methods available from the chemical literature (see for example for R =$R^1$==C$_6$H$_5$ and $R^3$=CO—C$_6$H$_5$, Beilstein 7 H 835 and foll.).

A synthesis process useful for preparing the compounds of formula II consists in reacting, according to a condensation type known in itself in literature (see for example the bibliographic reference cited hereinbefore), a proper methyl-ketone of formula $R^1$—CO—$R^3$, according to the following equation:

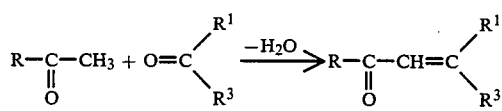

The reaction is conducted by heating the mixture of the two ketones in the presence of a base, preferably alcoholic potash.

A more general process for preparing the compounds of formula II consists in reacting the proper glyoxal

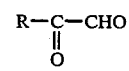

with a compound having an active methylene group according to the following equation:

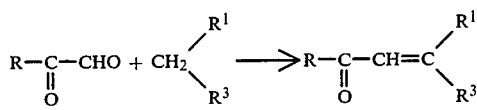

An alternative synthesis for preparing the compounds of formula I consists in reacting an α-halo-ketone of formula:

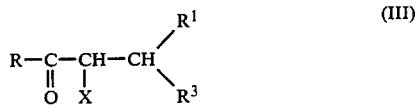

(wherein X = Cl, Br) with 1, 2, 4-triazol in the presence of a base, according to reaction 2:

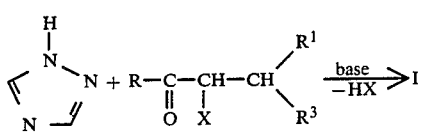

Reaction (2) is conducted in an inert solvent (for example tetrahydrofuran) in the presence of a stoichiometric amount of an inorganic or organic base (for example triethylamine) and at a temperature ranging from the room temperature and the boiling temperature of the reaction mixture.

The α-halo-ketones of formula III are preparable by halogenation of the compounds of formula IV according to the following reaction:

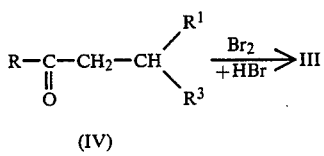

[see for example Chi-Kang Dien et al, J. Org. Chem. 21, 1492 (1956)].

The compounds of formula IV are prepared in turn according to methods which are known in literature, for example by reaction between an α-haloketone of formula V with a compound having an activa methylene group of formula IV according to reaction.

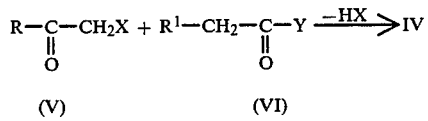

(wherein X = Cl, Br and

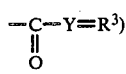

This reaction is conducted by reacting the compound of formula IV with sodium ethylate in ethyl alcohol at reflux temperature and by adding then, at room temperature, the compound of formula V. Both the compounds of formula V and the compounds of formula VI are known compounds or compounds easily preparable according to conventional techniques.

A third process for the synthesis if the compounds of formula I consists in reacting the proper α-triazolyl-ketone in the form of a sodium salt (VII) with a bromine derivative (VIII) according to the following equation:

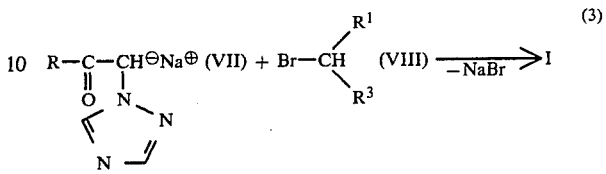

A synthesis method suitable for obtaining the compounds of general formula (I), wherein $R_1$ and $R_2$ form together an alkylidene group $=CHR^4$, R and $R^3$ may have all the meanings indicated hereinabove, is the following:

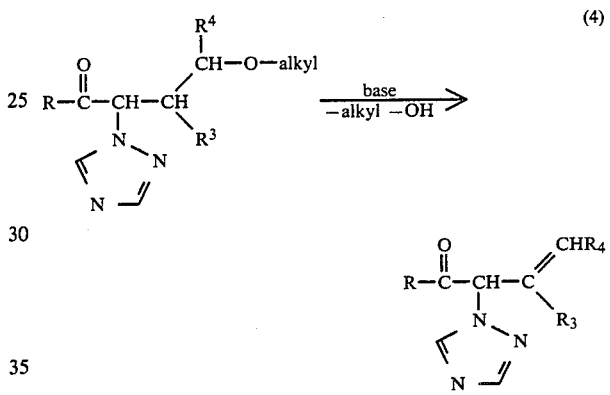

Reaction (4) is preferably conducted in an aprotic polar solvent, such as, e.g. DMF, at temperatures ranging from 0° to 20° C., by progressively adding to the solution of compounds (IX) a strong base such as for example an alkaline base, preferably sodium hydride, in a stoichiometric amount.

As is apparent to those skilled in the art, the compounds of formula I may exist in different isomeric forms due to the presence of asymmetry centres.

The preparation carried out according to the methods described hereinbefore generally provides mixtures of isomers of the compounds of formula I.

As previously mentioned, the compounds of formula I are endowed with a high fungicidal activity. They possess a wide range of action as they are active against phytopatogenous fungi belonging to a different genera of several families such as e.g. Plasmopara, Peronospora, Pythium, Pericularia, Puccinia, Erysiphe, Sphaerotheca, Botrytis, Phytophtora, Venturia, Fusarium and still others.

The compounds of formula I are therefore useful to fight several deseases of the plants, and prove to be particularly active against those deseases, which are commonly defined as oidium and rust.

As oidium-preventing agents the compounds of the invenition prove to be endowed with a very high or complete activity even at doses at which the compounds according to British Pat. No. 1,511,936 prove to be thoroughly inactive.

The compounds of the invention possess furthermore further positive characteristics, such as a fungicidal action whether of preventive or curative nature and a complete tolerance with the plants to be protected from the infection due to fungi.

Thanks to the high fungicidal activity connected to the positive characteristics mentioned hereinbefore, the fungicidal compounds may be employed in the defence of a large number of useful cultures from the fungi attack; among these there may be cited: vines, rice, gramineae, tomatos, tobacco and other Solanaceae, horticultures strawberries, Cucurbitaceae, fruit trees and ornamental plants. They are also utilized in the defence of food-stuff.

For the practical uses in agriculture it is often useful to have available fungicidal compositions containing one or more compounds of formula I as an active substance.

Said compositions which, according to the usual formulative practice, are in the form of dry powders, wettable powders, emulsifiable concentrates, pastes, granulated formulations and the like, consist of one or more compounds of formula I as an active principle, of a solid or liquid carrier and optionally of other additives such as e.g. surfactants, wetting agents, dispersants, suspending agents, etc.

If so desired, it is possible to add to the compositions forming the object of this invention also other active substances consistent therewith, such as fungicides, herbicides, phyto-grow regulators, fertilizers and insecticides.

The dose of active principle to be utilized varies as a function of different factors, among which the type, the degree and the stage of the infaction due to fungi, the culture to be protected, the relative effectiveness of the compound of formula I taken into consideration, climatic and environmental factors.

In general, due to the high fungicidal activity of the compounds of formula I, amounts of active compound ranging from 10 to 2000 g/ha, preferably from 100 to 1500 g/ha, are sufficient.

The following examples are given with a view to better illustrating the present invention.

EXAMPLE 1

Preparation of compound [α-(1, 2, 4-triazol-1-yl)-β-phenyl-β-benzoyl]-ethyl-4-phenylphenyl-ketone

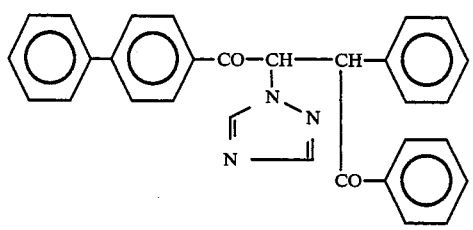

A mixture consisting of:
4.2 g of 1, 2, 4-triazol
15.7 g of 4-phenylphenyl-β-benzoyl-β-phenylvinyl-ketone

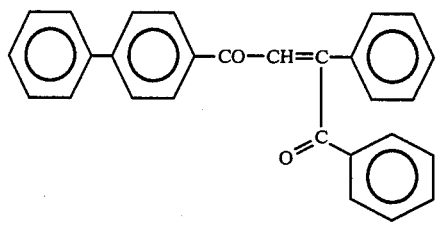

(prepared as is described in J.A.C.S. 52 (1930) 324, 386)
0.5 ml triethylamine
120 ml of toluene
was heated at reflux during 48 hours.

After cooling to room temperature, the mixture was washed with water and anhydrified on anhydrous sodium sulphate. After removal of the solvent by evaporation at reduced pressure, the rough product was subjected to chromatography on a silica gel (eluent: n.hexane-ethyl acetate in a ratio of 7 to 3).

4.2 g of the desired product (white solid, melting point 186°–187° C. after crystallization from isopropyl alcohol) were so obtained.

IR (nujol): significant bands at 1690, 1680, 1602 and 1580 cm$^{-1}$.
($\nu$C=O).

EXAMPLE 2

Preparation of compound 1-(4-chlorophenyl)-2-[1-(1,2,4-triazolyl)]-3-methylen-5,5-dimethylhexan-1, 4-dione

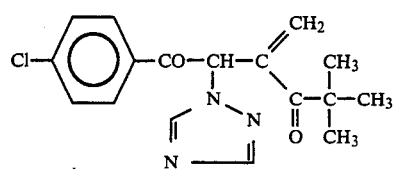

4 g of 1-(4-chlorophenyl)-2-[1-(1,2,4-triazolyl)]-3-propoxymethyl-5,5-dimethylhexan-1,4-dione

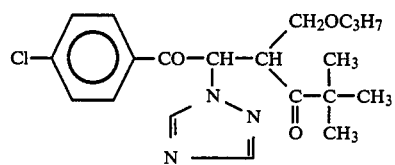

prepared according to method (3) and having the following characteristics: appearance: colourless oil
IR (nujol): significant bands at 1675, 1595, 1585, 1500, 1450 and 1400 cm$^{-1}$.
$^1$H-NMR (CDCl$_3$, TMS) δ(ppm): 8.5–6.7 (m, 6 H, aromatic protons) 5.1–5.5 (m, 1 H), 5.5–4 (m, 1 H), 4–3.3 (m, 2 H), 3.3–2.9 (tripl. 2 H), 1.5–0.5 (m, 5 H) were dissolved in 30 ml of anhydrous DMF. This solution was treated in small proportions with 0.5 g of NaH (suspension in oil at 50%), maintaining a temperature from 0° to 5° C.

After one hour at room temperature, the reaction mixture was poured into water, the resulting precipitate was filtered and was crystallized from isopropyl alcohol. The desired product having a melting point of 145° C. was obtained.

IR (nujol): significant bands at 1688, 1665, 1595, 1580 and 1500.

EXAMPLES 3 to 7

By operating according to the methods described in the equations from 1 to 4, the compounds indicated in the following Table 1 and corresponding to general formula (I) were obtained.

The data relating to the fungicidal activity against cucumber oidium exerted by certain compounds of formula I as compared with a compound according to British Pat. No. 1,511,956 are shown in the following Table 2.

TABLE 1

| Ex. No. | R | $R^1$ | $R^2$ | $R^3$ | m.p. °C. | IR $cm^{-1}$ |
|---|---|---|---|---|---|---|
| 3 | $4\text{-}C_6H_5\text{-}C_6H_4\text{-}$ | $-CH_3$ | H | $-\overset{O}{\underset{\|\|}{C}}-C(CH_3)_3$ | 88–90 | 1710,1665,1495,1430 |
| 4 | $4\text{-}C_6H_5\text{-}C_6H_4\text{-}$ | $-C_6H_5$ | H | $-\overset{O}{\underset{\|\|}{C}}-C(CH_3)_3$ | 134–135 | 1702,1595,1490,1430 |
| 5 | $4\text{-}Cl\text{-}C_6H_4\text{-}$ | $-OCH_3$ | H | $-\overset{O}{\underset{\|\|}{C}}-C(CH_3)_3$ | 187–188 | 3220,3100,1730,1620 1590 |
| 6 | 2-furile | $4\text{-}Cl\text{-}C_6H_4\text{-}$ | H | $-\overset{O}{\underset{\|\|}{C}}-C(CH_3)_3$ | olio | 1705,1673,1580,1530 |
| 7 | $2,4\text{-}Cl_2\text{-}C_6H_3\text{-}$ | $\{=CH_2$ | | $-\overset{O}{\underset{\|\|}{C}}-C_6H_5\}$ | 161–163 | 1690,1665,1590,1505 |

Note:
The elemental analysis and the $^1$H—NMR spectroscopy data of all the compounds of examples 1 through 7 are consistent with the assigned structure. The melting points of the resulting compounds have not been corrected.

EXAMPLE 8

Determination of the fungicidal action against cucumber oidium [*Sphaerotheca fuliginea* (Schlech) Salmon].

Preventive action:

Cucumber plants cv. Marketer, grown in pots in a conditioned ambient, were sprayed, on the lower faces of their leaves, with the product being tested in a hydroacetonic solution at 20% of acetone (vol./vol.). The plants were then kept in a conditioned environment during 6 days and on the 7th day the upper faces of their leaves were sprayed with an aqueous suspension if conids of *Sphaerotheca fuliginea* (200,000 conids/ml). The plants were then brought again to a conditioned environment.

At the conclusion of the fungus incubation period (8 days), the infection degree was evaluated through indexes of an evaluation scale from 100 (=sound plant) to 0 (=fully infected plant).

Curative activity:

Cucumber plants cv. Marketer, grown in pots in a conditioned environment, were sprayed on the upper faces of their leaves with an aqueous suspension of conids of *Sphaerotheca fuliginea* (200,000 conids/ml). 24 hours after the infection, the plants were treated with the product being tested in a hydroacetone solution at 20% of acetone (vol./vol.) by spraying it onto both leaf faces.

At the end of the fungus incubation period (8 days), during which the plants were maintained in a properly conditioned environment, the infection degree was evaluated according to indexes of an evaluation scale from 100 (=sound plant) to 0 (=fully infected plant).

TABLE 2

Fungicidal activity against cucumber oidium at the indicated doses expressed by means of a scale from 100 (=sound plant) to 0 (fully infected plant).

| Compound | Dose | Preventive |
|---|---|---|
| Example No. | g/l | activity |
| 1 | 0.5 | 95 |
| 2 | 0.5 | 100 |
|   | 0.25 | 100 |
|   | 0.125 | 100 |
|   | 0.06 | 100 |
| 3 | 0.5 | 100 |
|   | 0.25 | 100 |
|   | 0.125 | 100 |
|   | 0.06 | 100 |
| 4 | 0.5 | 100 |
|   | 0.25 | 100 |
|   | 0.125 | 100 |
|   | 0.06 | 100 |
| 5 | 0.5 | 90 |
| 6 | 0.5 | 100 |
|   | 0.25 | 50 |
| 7 | 0.5 | 100 |
|   | 0.25 | 100 |
|   | 0.125 | 100 |
| Ref.* | 0.5 | 90 |
|   | 0.25 | 50 |
|   | 0.125 | 10 |
|   | 0.06 | 0 |

*As a check there was utilized the compound 2-(1,2,4-triazol-1-yl)-1,4(di-4-chlorophenyl)-butan-1,4-dione of formula:

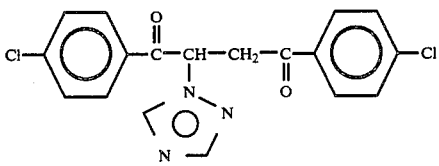

described in example 1 of British patent No. 1,511,956.

What we claim is:
1. Compounds of formula:

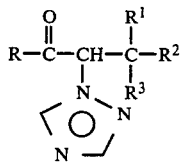

in which:
- R is a phenyl optionally substituted by at least one group selected from alkyl $C_1$-$C_4$, alkynyl and haloalkynyl $C_2$-$C_3$, halogen, nitro and phenyl;
- $R^1$ represents, together with $R^2$, an alkylidene of formula ($=CHR^4$), wherein $R^4$ is selected from hydrogen and alkyl $C_1$-$C_4$;
- $R^3$ is an alkyl carbonyl $C_1$-$C_4$ in the alkyl moiety; an aryl carbonyl in which the aryl moiety is phenyl optionally substituted by at least one group selected from alkyl $C_1$-$C_4$, alkynyl or haloalkynyl $C_2$-$C_3$, halogen, nitro, phenyl; an alkoxyalkylcarbonyl having from 1 to 4 carbon atoms in both the alkyl and in the alkoxyl moiety.

2. Compounds according to claim 1 in which $R^3$ is selected from the group consisting of alkyl carbonyl having from 1 to 4 carbon atoms, phenylcarbonyl and halophenylcarbonyl.

3. Compounds according to claim 1 in which R is selected from the group consisting of halogenphenyl and dihalogenphenyl;

$R^3$ is selected from the group consisting of alkylcarbonyl having from 1 to 4 carbon atoms, phenylcarbonyl and halophenylcarbonyl.

4. A method of controlling infections due to fungi in useful plants against the infections caused by the fungi known as oidium and rust, consisting in distributing onto the plants or in the area in which they grow, when the infection caused by fungi is expected or is already in progress, an effective amount of a compound according to claim 1, either as such or as a composition suitable for agrarian use.

5. A compound of formula:

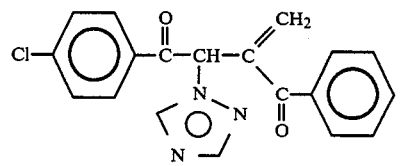

6. A compound of formula:

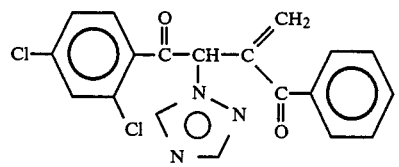

* * * * *